(12) United States Patent
Tseng et al.

(10) Patent No.: US 6,730,117 B1
(45) Date of Patent: May 4, 2004

(54) INTRALUMINAL STENT (75) Inventors: David Tseng, Santa Rosa, CA (US); Ellen Golds, Hastings-on-Hudson, NY (US); Bruce Parsons, Pompano Beach, FL (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/623,347
(22) PCT Filed: Mar. 4, 1999
(86) PCT No.: PCT/US99/04694
§ 371 (c)(1), (2), (4) Date: Nov. 15, 2000
(87) PCT Pub. No.: WO99/44535
PCT Pub. Date: Sep. 10, 1999

Related U.S. Application Data

(60) Provisional application No. 60/076,946, filed on Mar. 5, 1998.

(51) Int. Cl.⁷ .................................................. A61F 2/06
(52) U.S. Cl. ..................................... 623/1.16; 623/1.22
(58) Field of Search .............................. 623/1.15, 1.16, 623/1.22, 1.17, 1.18, 1.19, 1.2

(56) References Cited

U.S. PATENT DOCUMENTS

| 4,512,338 A | 4/1985 | Balko et al. |
| 4,856,516 A | 8/1989 | Hillstead |
| 4,886,062 A | 12/1989 | Wiktor |
| 4,994,071 A | 2/1991 | MacGregor |
| 5,019,090 A | 5/1991 | Pinchuk |
| 5,035,706 A | 7/1991 | Giantureo |
| 5,102,417 A | 4/1992 | Palmaz |

(List continued on next page.)

FOREIGN PATENT DOCUMENTS

| EP | 480 667 | 4/1992 |
| EP | 734 699 | 10/1996 |
| EP | 0801 934 A2 | * 10/1997 |
| EP | 801 934 | 10/1997 |
| EP | 807 424 | 12/1997 |
| EP | 540 290 | 1/1998 |
| EP | 0 662 307 | 5/1998 |
| WO | WO 93/13825 | 7/1993 |
| WO | WO 96/41590 | * 12/1996 |
| WO | WO 97/09945 | 3/1997 |
| WO | WO 98/20810 | 5/1998 |

*Primary Examiner*—David H. Willse
*Assistant Examiner*—Hieu Phan
(74) *Attorney, Agent, or Firm*—RatnerPrestia (57) ABSTRACT

This invention is an intraluminal stent (10) made of a zigzag or sinusoidal member defining a successive series of struts (14) connected by apex sections (15), and formed into a series of axially displaced hoop members (12a–12n) wherein at least one of the hoop members has at least one strut (14) connected to a strut (14) of an adjacent hoop. The connected struts (14) may be connected by spot welding, continuous welding, or suturing, for example, or by a bridging member (26) connected to each strut (14), and may be spaced along the length of the stent in a pattern to form a connective spine (16). The number of zigs of the zigzag member in each hoop member (12a–12n) may be varied, as can the zig length (L1). A plurality of connective spines (16) may also be included.

55 Claims, 9 Drawing Sheets

U.S. PATENT DOCUMENTS

| | | |
|---|---|---|
| 5,104,404 A | 4/1992 | Wolff |
| 5,133,732 A | 7/1992 | Wiktor |
| 5,135,536 A | 8/1992 | Hillstead |
| 5,195,984 A | 3/1993 | Schatz |
| 5,201,901 A | 4/1993 | Harada et al. |
| 5,217,483 A | 6/1993 | Tower |
| 5,282,824 A | 2/1994 | Gianturco |
| 5,292,331 A | 3/1994 | Boneau |
| 5,354,309 A | 10/1994 | Schnepp-Pesch et al. |
| 5,370,683 A | 12/1994 | Fontaine |
| 5,405,377 A | 4/1995 | Cragg |
| 5,421,955 A | 6/1995 | Lau et al. |
| 5,443,498 A | 8/1995 | Fontaine |
| 5,449,373 A | 9/1995 | Pinchasik et al. |
| 5,507,767 A | 4/1996 | Maeda et al. |
| 5,514,154 A | 5/1996 | Lau et al. |
| 5,549,663 A | 8/1996 | Cottone, Jr. |
| 5,569,295 A | 10/1996 | Lam |
| 5,575,816 A | 11/1996 | Rudnick et al. |
| 5,603,721 A | 2/1997 | Lau et al. |
| 5,626,599 A | 5/1997 | Bourne et al. |
| 5,649,952 A | 7/1997 | Lam |
| 5,653,727 A | 8/1997 | Wiktor |
| 5,674,278 A | 10/1997 | Boneau |
| 5,707,386 A | 1/1998 | Schnepp-Pesch et al. |
| 5,716,396 A | 2/1998 | Williams, Jr. |
| 5,728,158 A | 3/1998 | Lau et al. |
| 5,735,893 A | 4/1998 | Lau et al. |
| 5,766,238 A | 6/1998 | Lau et al. |
| 5,800,456 A | 9/1998 | Maeda et al. |
| 5,800,508 A | 9/1998 | Goicoechea et al. |
| 5,800,515 A * | 9/1998 | Nadal et al. ................ 623/1.15 |
| 5,800,519 A | 9/1998 | Sandock |
| 5,968,091 A | 10/1999 | Pinchuk et al. |
| 6,136,023 A | 10/2000 | Boyle |
| 6,368,346 B1 * | 4/2002 | Jadhav .................... 264/210.8 |
| 6,383,216 B1 * | 5/2002 | Kavteladze et al. ....... 623/1.15 |

* cited by examiner

INTRALUMINAL STENT

This application is a U.S. National Phase application of PCT International Application No. PCT/US99/04694.

CROSS-REFERENCE TO RELATED APPLICATIONS

This invention claims priority based on U.S. Provisional Application Ser. No. 60/076,946, filed Mar. 5, 1998, which is hereby incorporated by reference.

FIELD OF THE INVENTION

This invention relates generally to intraluminal prostheses, and more particularly to intraluminal stents comprised of zig-zag or sinusoidal wire hoops.

BACKGROUND OF THE INVENTION

A common method of treating vessel diseases such as stenoses, strictures, thrombosis, or aneurysms involves placing a stent into the affected vessel. Among other advantages, stents prevent vessels from collapsing, reinforce vessel walls, increase cross sectional area (and thereby volumetric flow), and restore or maintain healthy blood flow. Many stents have been developed, and the prior art includes a wide variety of types and methods for their manufacture.

SUMMARY OF THE INVENTION

The present invention is a generally cylindrical intraluminal stent including a plurality of circumferential wire hoops disposed in succession along the axis of the stent. Each of the hoops has zig-zag or sinusoidal members defied by a successive series of struts connected by apex sections alternately pointing in opposite axial directions. The struts may be substantially straight sections connected to essentially sharp apex sections in a jagged zig-zag configuration, or the apex sections may be more rounded so that together with the struts there is formed a sinusoidal configuration. The lengths of these struts may be uniform throughout the stent or may vary alternately or continuously. Likewise, the angles or radii of curvature and configurations of the apices may be uniform or may vary. To provide mechanical integrity, selected portions of the hoops may be secured against relative axial movement, such as by spot welding overlying straight sections either in an individual hoop or in adjacent hoops. Such connections may also be made with bridging members aligned with straight sections in adjacent hoops.

These connections (with or without intervening bridging members) may be disposed in one or more linear or helical paths along the length of the stent, thus acting as stabilizing spines. Alternatively, these connections may be disposed in other preselected patterns, such as alternating around the circumference of the stent, to impart stability at these preselected locations.

BRIEF DESCRIPTION OF THE DRAWINGS

The figures provided are for illustrative purposes, and are not drawn to scale. The expanded relative dimensions allow a better understanding of the present invention. One skilled in the art will readily determine actual dimensions based on information supplied in this specification.

DETAILED DESCRIPTION OF THE INVENTION

Figure 1:
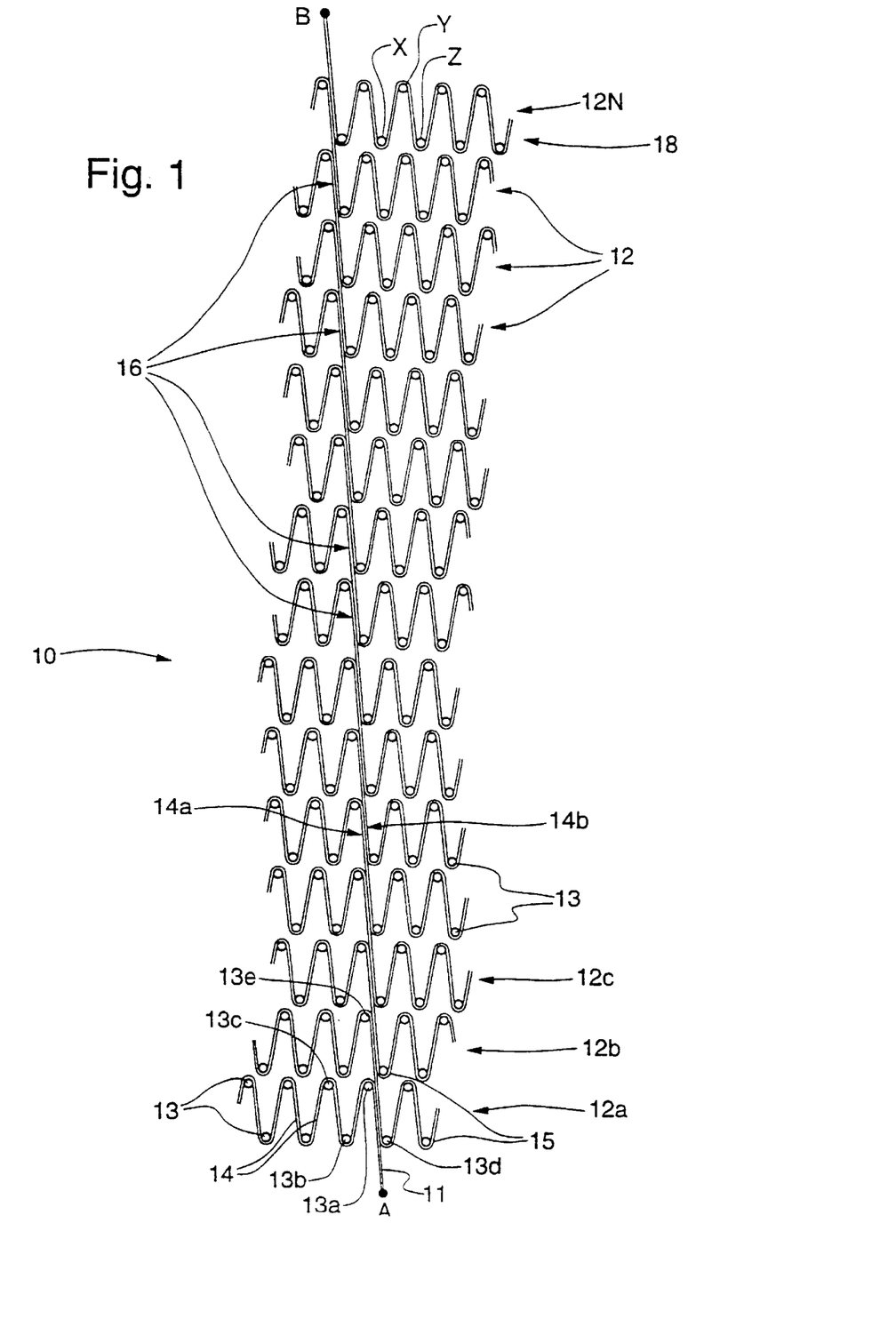
FIG. 1 is a diagrammatic view of an exemplary embodiment of a stent according to this invention, where the tubular stent is shown opened along a line parallel to the stent axis, and flattened; also shown are mandrel pins used in forming the stent.

FIG. 1 illustrates an exemplary stent 10 according to the present invention. Stent 10 is generally cylindrical and adapted to be inserted into a lumen. Stent 10 has been cut longitudinally and laid flat for purposes of illustration. Stent 10 is formed by winding a continuous filament such as a wire 11 into a zig-zag or sinusoidal configuration and into a plurality of circumferential hoop members 12a, 12b, 12c disposed in succession along the axis of stent 10. Wire 11 is preferably nitinol wire, which provides a stent that auto-expands by shape memory, but it may be made of any suitable material, including stainless steel and thermoplastic polymers. Thus, the stent may be capable of deployment by shape memory auto-expansion, thermal auto-expansion or balloon expansion, as are well-known in the art. The width of the wire affects the radial force exerted by stent 10. Increasing the diameter of wire 11 increases the radial force.

For convenience, the configuration of the wire is referred to throughout having a "zig-zag" shape with zigs or zig lengths. As so used herein, however, the term "zig-zag" encompasses not only a jagged zig-zag shape where the apex sections are relatively sharp and the struts are substantially straight, but also a sinusoidal shape where the apex sections are rounded and, together with the struts, form a shape resembling a sine wave having an amplitude (zig length) and a period or wavelength (zig width). Similarly, although the apex sections may be referred to as defining a zig angle, the angle may be more rounded such that lesser and greater angles may be more envisioned as smaller and larger radii of curvature, respectively. Of course, the actual wire configuration may have a shape intermediate the jagged zig-zag and rounded sine wave shapes, or may be even more rounded than a sine wave, and the apex sections may in fact have a truncated, straight edge rather than a rounded shape or sharp angle, as described herein later.

To form stent 10, wire 11 is wound around pins 13 on a mandrel (not shown). The mandrel is typically cylindrical (although other shapes may be used as necessary to form stents of varying shapes) and of a diameter determined by the diameter of the vessel into which stent 10 is to be inserted. Typically, the mandrel diameter, and hence the intended diameter of stent 10, is slightly larger (for example, by one millimeter) than the diameter of the vessel. The length of stent 10 is also determined by the particular application.

Stent 10 is formed by winding wire 11 around pins 13 beginning at point A in FIG. 1. Wire 11 is extended to and around pins 13a, 13b, 13c and so forth. In this manner, zig-zag members are formed and defined by a successive series of substantially straight sections (struts) 14 connected by apex sections 15 alternately pointing in opposite axial directions. The winding continues in this manner around the mandrel until a first hoop member 12a is completed by winding wire 11 once around the circumference of the mandrel. Hoop member 12a as shown in FIG. 1 has a circumference lying in a plane substantially perpendicular to the axis of the mandrel (and hence of stent 10). Once a first hoop member 12a is formed, wire 11 is extended from pin 13d to and around pin 13e. Winding then continues as before to form a second hoop member 12b adjacent to first hoop member 12a. By forming hoop members in this manner, adjacent hoops 12a and 12b are connected by the portion of wire 11 extending between first hoop member 12a and second hoop member 12b. At the completion of the second hoop member 12b, wire 11 is again extended to the third hoop member 12c, which is wound as before, and so forth until the desired number N of hoop members 12 are formed along the length of stent 10. Thus, as shown in FIG. 1, the winding extends in a series of hoops between hoops 12a and hoop 12N, with the wire beginning at point A and ending at point B. After completion of winding, wire 11 is typically cut so that the wire terminates short of points A and B, generally terminating within the first hoop 12a and last hoop 12N, respectively, as described with reference to FIG. 6C herein later.

Stent 10 is removed from the mandrel and pins 13a, 13b, 13c, etc., prior to use. In the illustrated embodiment, each hoop member 12 has one pair of aligned, adjacent struts 14a and 14b. According to one embodiment of the present invention, aligned, adjacent struts 14a and 14b of the same hoop are welded together. Such welding may be spot welding along the length of aligned, adjacent struts 14a and 14b, or it may be a continuous weld. In either case, a welded, connective spine 16 is formed along the perimeter of stent 10. Connective spine 16 typically winds around the circumference of stent 10 in an offset helical fashion (the embodiment shown flat in FIG. 1 being cylindrical or tubular in actual use). Connective spine 16 provides strength and stability to stent 10 while preserving the flexibility of stent 10. During insertion of stent 10 into a vessel (described below), connective spine 16 renders stent 10 easier to push through a catheter. As an alternative to welding, connective spine 16 may be formed by connecting aligned, adjacent struts 14a and 14b according to any other suitable attachment means, including without limitation, tying, suturing, gluing, and stapling, with the glue or sutures being absorbable or non-absorbable, and including the use of polymer-containing connections.

When stent 10 comprises thermally expandable nitinol, stent 10 is annealed before removal from the mandrel and pins 13a, 13b, 13c, etc., at an annealing temperature for about one hour and then allowed to cool. This annealing temperature is desirably on the order of about 500° C., although any temperature sufficient to effect annealment of stent 10 will suffice. During annealing, it may be necessary to secure the nitinol wire to the mandrel by wrapping bailing wire, a thicker gauge and different material than the nitinol, around the stent on the mandrel. Such annealing of nitinol wire imparts a memory to the nitinol, such that stent 10 will "remember" its annealed shape and return to it after subsequent reconfiguration. This is a known property of nitinol, which has two distinct temperature-dependent phases, martensite and austenite. Below a certain temperature (the martensite transition temperature), nitinol is martensitic; above a certain temperature (the austenite transition temperature), it is austenitic. It is in the austenitic phase that nitinol remembers its annealed configuration.

After annealing, stent 10 is removed from the mandrel on which it is wound to compress stent 10 into a configuration for introduction to a body passageway. Then, it is cooled to below its martensitic transition temperature. In this phase, nitinol is malleable and has virtually no resiliency. Thus, it can be easily compressed. Stent 10 can be easily returned to its annealed shape by heating it to a temperature above its austenite transition temperature. Above this temperature, the stent resumes its annealed configuration.

In its annealed configuration, stent 10 has a first diameter. This is a relatively large diameter that is the intended final diameter of stent 10. In order to be inserted into a body vessel, stent 10 must be compressed such that it may be inserted into a catheter. As indicated above, with a nitinol stent, this is accomplished by cooling stent 10 to below its martensite transition temperature at which temperature stent 10 is malleable and less resilient. Stent 10 can then be easily compressed into a second, relatively small diameter for insertion into the catheter. Once inside the catheter, stent 10 may be advanced to the desired location within a body vessel according to methods known in the art and discharged from the catheter at that location. U.S. Pat. Nos. 5,405,377 and 5,609,627, the disclosures of which are incorporated herein by reference, contain additional details regarding the formation, use, and insertion of nitinol stents. Those patents are incorporated herein by reference for their teaching on those subjects. When stainless steel, thermoplastic polymers, or other materials are used for wire 11, formation, use and insertion of stent 10 may be accomplished according to methods known to those skilled in the art.

Connective spine 16 lends strength, including hoop strength, to stent 10 during and after implantation to better resist compressive forces within the vessel in which stent 10 is implanted. Connective spine 16 also allows flexibility, however, such that stent 10 may be easily compressed and expanded during the insertion process.

Figure 2:
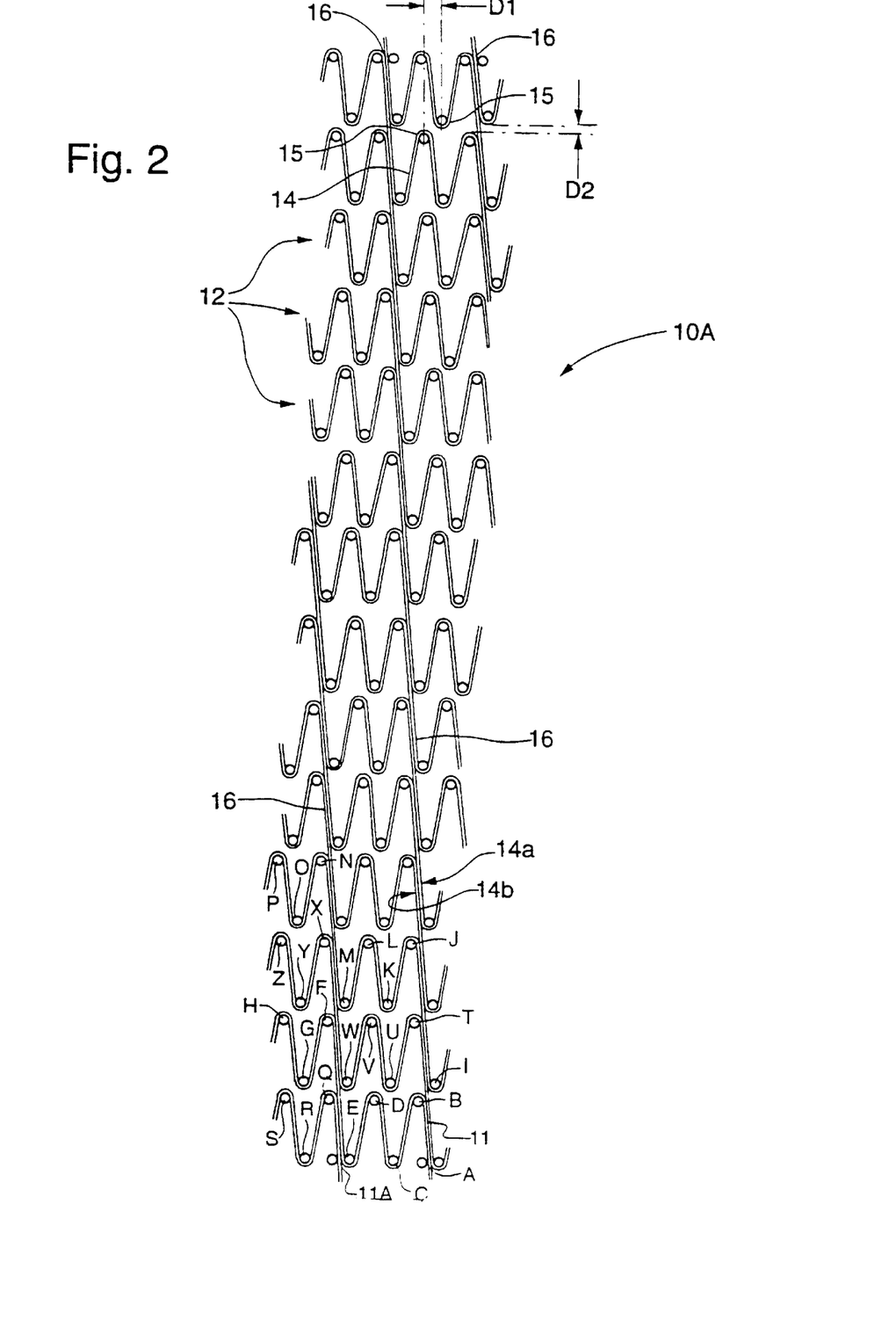
FIG. 2 is a diagrammatic view of another exemplary embodiment of a stent according to this invention having multiple spines and axial and circumferential offsets between facing apex sections, where the tubular stent is shown opened along a line parallel to the stent axis, and flattened; also shown are mandrel pins used in forming the stent.

Particular features of the stent according to this embodiment of the invention are illustrated in FIG. 2. As shown in FIG. 2, facing apex sections 15 of respective adjacent hoops of stent 10A are offset circumferentially from one another by a distance D1, as opposed to abutting one another. The offset allows stent 10A to be compressed to a smaller diameter (profile) for insertion into the catheter because the apex sections do not contact one another and hinder such compression. Increasing the axial distance D2 between apex sections 15 (the "zig gap") also prevents interference between these sections during compression. The particular amount of offset and zig gap can be optimized according to particular stent sizes and the desired flexibility and compressed diameter as will be understood by those skilled in the art.

Figure 3:
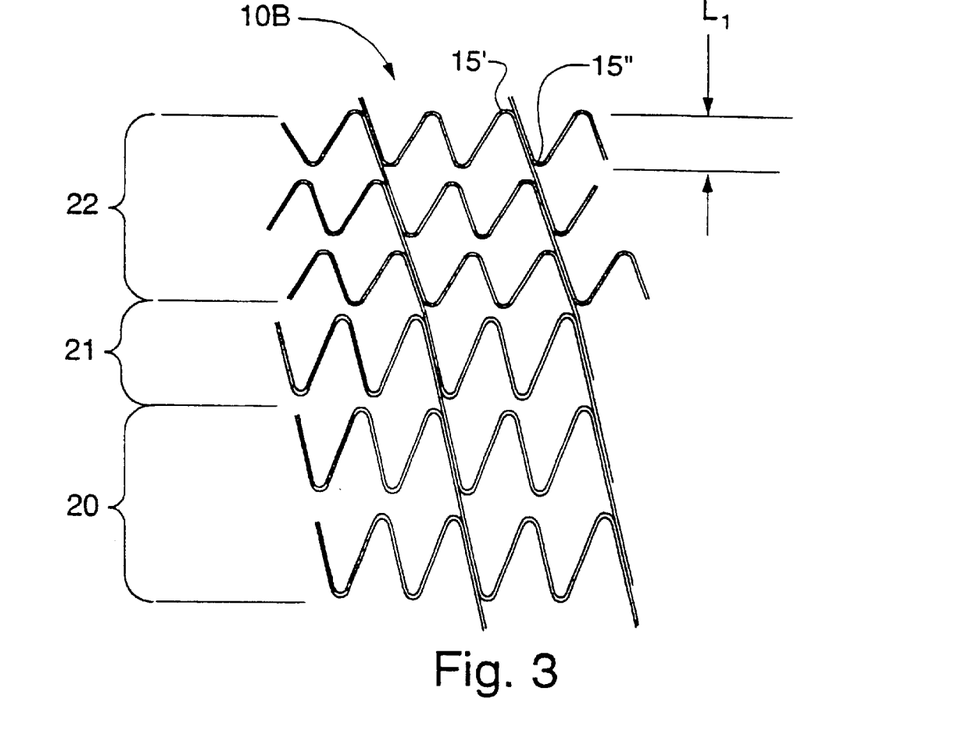
FIG. 3 is a partial diagrammatic view of another exemplary embodiment of a stent according to this invention having a plurality of longitudinal sections, the middle section having a different number of spines, a different number of zigs, and a different zig length than the end sections, where the tubular stent is shown opened along a line parallel to the stent axis, and flattened.

FIG. 2 also illustrates an embodiment of this invention having multiple, in this case two, connective spines 16. To form two connective spines 16, two separate wires 11 and 11A are used to form stent 10A. As shown in FIG. 3, first wire 11 is formed in a zig-zag shape extending from point A to points B, C, D, E, F, G, H, I, J, K, L, M, N, O, P (etc.) sequentially. A second wire 11A is used to form the remainder of the stent by extending, in sequence from point E to points Q, R, S, A, T, U, V, W, X, Y, Z (etc.). In this manner, each hoop contains two pairs of aligned, adjacent struts 14a and 14b. Aligned, adjacent struts 14a and 14b are then welded (or otherwise connected) to form connective spines 16. In general, the number of wires 11, 11A, etc. used to form stent 10A directly corresponds to the number of connective spines 16 that are desired. The strength and rigidity of stent 10A increase with the addition of connective spines 16.

In the above configuration, the mandrel peg at each lettered point may be considered to be one of a set of pegs corresponding to the wire to wound about the set. Thus, pegs at points A, B, C, etc. above are a part of one set, and pegs E, Q, R, etc. above are part of a second set. Each set, however, contains at least one common peg (for example, F in the first set and W in the second set) where both wires follow a common path between the common pegs of the circumferentially adjoining sets. The wires that form the common path (adjacent struts 14a and 14b) are connected as described above.

FIG. 3 illustrates another alternative embodiment of this invention wherein the zig length $L_1$ is varied within stent 10B. Zig length $L_1$ is the distance between apex sections 15' and 15" measured in a direction parallel to the stent axis (vertical, in FIG. 3). As previously indicated, the zig length may similarly be described as the amplitude of a sinusoidally shaped zig-zag. In this embodiment, the zig length at end sections 22 of stent 10B may be relatively short (relatively small amplitude), while the zigs in middle section 20 of stent 10B are relatively long (having greater amplitude). This may provide greater radial force at the ends of stent 10B to assist in anchoring the stent in place in the vessel into which it is inserted by asserting a greater force against the walls of the vessel. This may also prevent blood from leaking between stent 10B (when the stent is used in combination with a graft, as will be understood by those skilled in the art) and the vessel wall.

As illustrated in FIG. 3, there may also be a transition section 21 in which there is a transition zig length, between the short zig length at the stent ends 22 and the long zig length in the stent middle 20, to provide a gradual transition from the short to the long zigs. Typical short zig lengths are between two and three millimeters. Typical long zig lengths are between three-and-a-half and five millimeters. The actual zig lengths may be optimized for particular applications as will be understood to those skilled in the art based on the disclosure herein.

Another aspect of this invention involves the variation of the number of zigs in each hoop member. Referring back to FIG. 1, a "zig" is considered to be the part of wire 11 extending from, for example, point X to point Y to point Z. X-Y-Z in FIG. 1 is considered to represent one zig. Thus, each similarly-oriented apex section (i.e. each apex section pointing in the same direction) defines a zig. As previously indicated, the number of zigs in a hoop may be similarly described as the number of periods of a sinusoidally shaped zig-zag. In FIG. 1, each hoop member has five zigs. Using fewer zigs allows stent 10 to be compressed to a smaller insertion diameter (that is, fewer zigs decreases the profile of stent 10). Increasing the number of zigs provides more support for any graft covering used in conjunction with the stent, however, preventing the possibility of in-folding of such graft layer.

Figure 4:
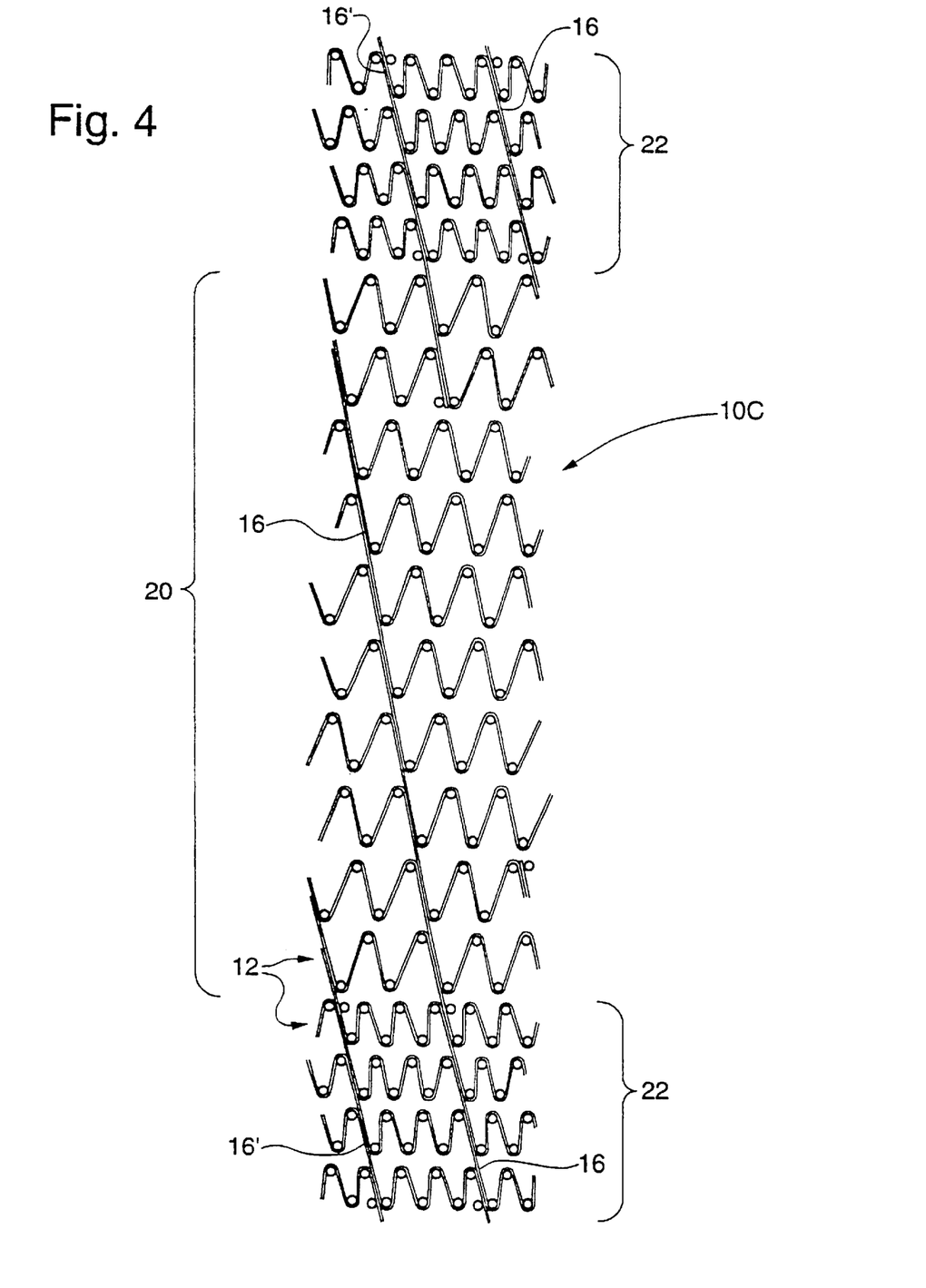
FIG. 4 is a diagrammatic view of another exemplary embodiment of a stent according to this invention having end portions with different zig characteristics relative to a center portion, where the tubular stent is shown opened along a line parallel to the stent axis, and flattened; also shown are mandrel pins used in forming the stent.

FIG. 4 illustrates an alternative embodiment, not drawn to scale, wherein the center portion 20 of stent 10 has four zigs per hoop member 12, a first zig length, and one connective spine 16; and the end portions 22 have six zigs per hoop member 12, a second zig length, and two connective spines 16. The second spines on both ends overlap two hoop members 12 of the center portion as a transition. The number of connective spines 16 can thus be varied within a stent to provide a more rigid portion at the ends and a more flexible portion in the middle. The stent illustrated in FIG. 8 may have, for example, a wire diameter of 0.007 inches, a 6.4 mm OD, a 6 mm ID, and a length of 100 mm. Other wire diameters slightly larger than 0.007 inches such as 0.008 or 0.009 inches, for example, will suffice.

Figure 9:
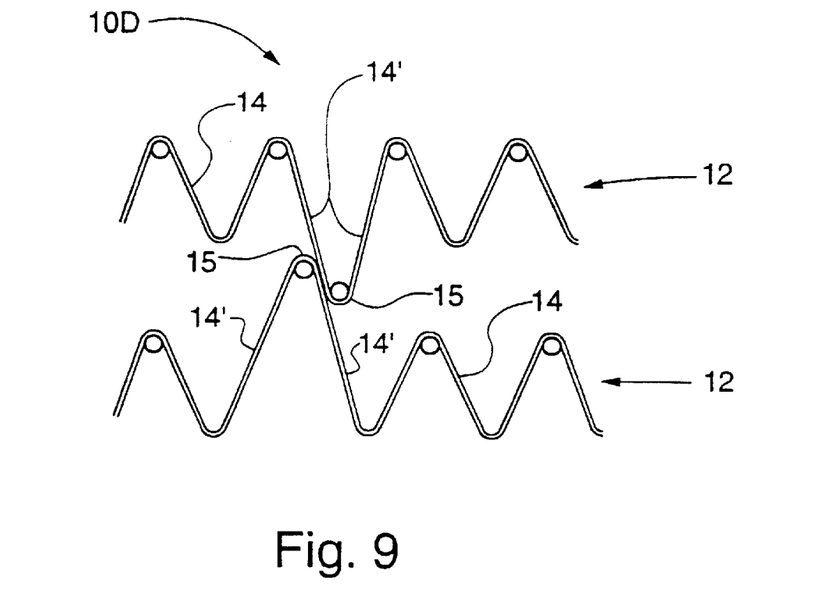
FIG. 9 is a partial diagrammatic view of another exemplary embodiment of a stent according to this invention having connecting members formed by elongated struts, where the tubular stent is shown opened along a line parallel to the stent axis, and flattened; also shown are mandrel pins used in forming the stent.

As shown in FIG. 9, another method of making connecting members may comprise axially opposed apex sections 15 of adjacent hoops 12 being axially spaced from one another with one or both of the first and second struts 14' of the connecting member elongated relative to the remainder of the struts 14 in the adjacent hoops. Such elongated struts 14' may thus lie adjacent one another for at least some axial distance to permit connection therebetween.

Figure 5:
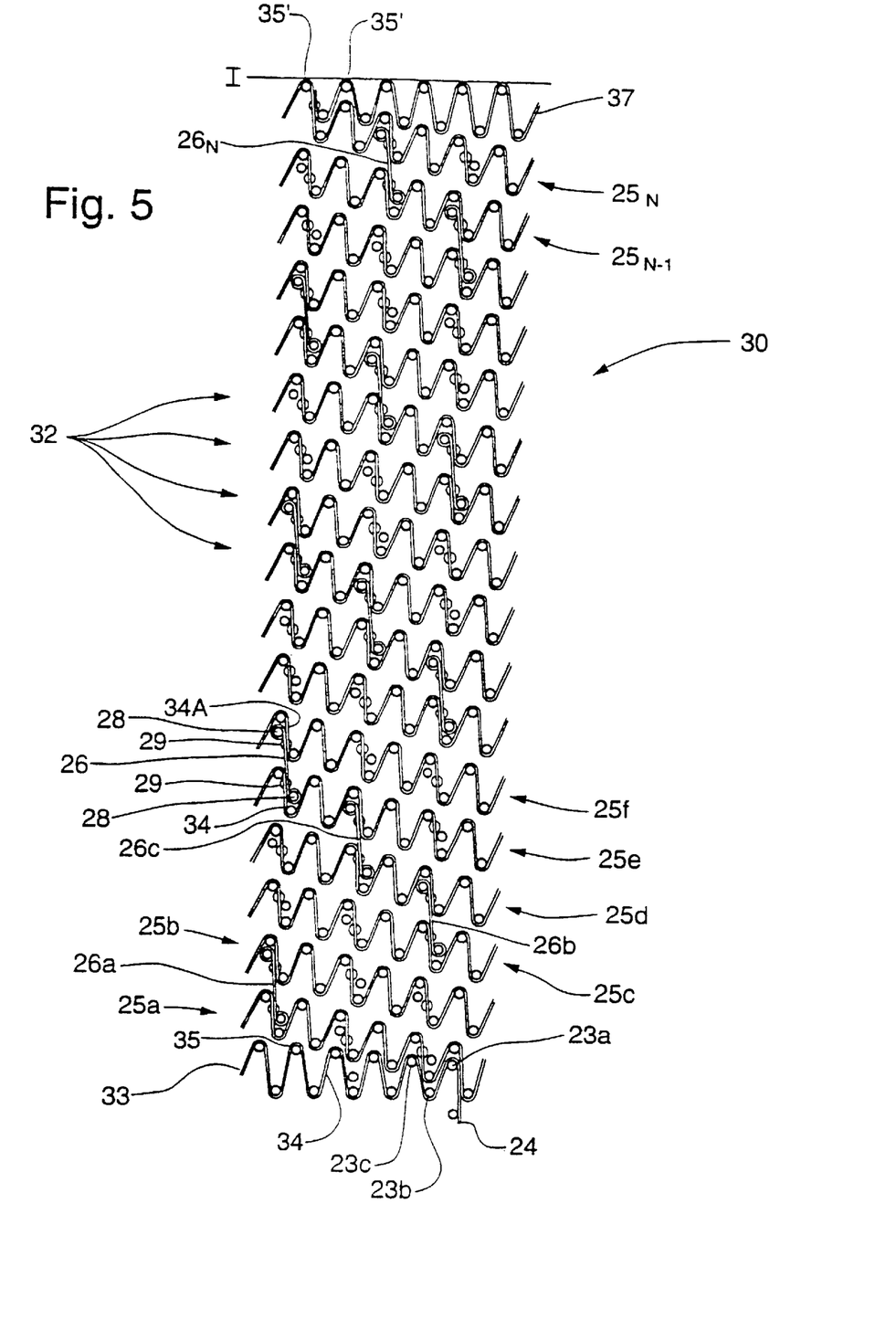
FIG. 5 is a diagrammatic view of another exemplary embodiment of a stent according to this invention having connecting members that include separate bridging members, where the tubular stent is shown opened along a line parallel to the stent axis, and flattened; also shown are mandrel pins and weld holes used in forming the stent.

FIG. 5 illustrates a stent constructed according to another exemplary embodiment of the present invention. Stent 30 is generally cylindrical and adapted to be inserted into a lumen. Stent 30 has been cut longitudinally and laid flat for purposes of illustration. Stent 30 is formed by winding a continuous filament such as a wire 24 into a zig-zag configuration and into a plurality of circumferential hoop members 33, 25a . . . 25N, and 37 disposed in succession along the axis of stent 30. Wire 24 is extended to and around pins 23a, 23b, 23c and so forth. In this manner, zig-zag members are formed and defined by a successive series of substantially straight sections 34 connected by apex sections 35 alternately pointing in opposite axial directions. The winding continues in this manner around the mandrel until a first hoop member 33 is completed by winding wire 24 once around the circumference of the mandrel. Winding then continues as before to form a second hoop member 25a adjacent to first hoop member 33 and a third hoop member 25b adjacent to second hoop member 25a. Unlike hoop members 12 of stent 10 as shown in FIG. 1, hoops 25a . . . 25N are disposed at an angle to a plane perpendicular to the stent longitudinal axis; wire 24 then gradually spirals about the axis of stent 30 to form a coil. End hoops 33 and 37, however, are disposed perpendicular to the stent axis. The helical configuration may be effected by each apex section in the helix having one connected strut longer than the other.

As further illustrated in FIG. 5, adjacent hoops are connected by a separate bridging member 26 adjacent portions of respective straight sections 34 and 34A of axially opposed apex sections of adjacent hoops. As illustrated in FIG. 5, bridging member 26 is preferably linear and aligned with aligned struts 34 and 34A of proximate sections of adjacent hoops $25_i$ and $25_{i+1}$, although non-linear and non-aligned bridging members are also contemplated in accordance with the present invention, as may be appreciated by those skilled in the art. Separate bridging member 26 may be the same material as or a different material than wire 24 used to form hoops 33, 25a–N, and 37 of stent 30, depending on the desired flexibility and compressed stent diameter. In one embodiment, separate bridging member 26 and wire 24 are made of the same material, for example, nitinol. Separate bridging member 26 and wire 24 may have approximately the same or different cross sectional dimensions (i.e. the same or a different wire gauge), depending on the desired implementation.

An exemplary separate bridging member 26 is preferably formed by extending a wire segment between a pair of pins 28 extending from the mandrel proximate straight sections 34 and 34A of adjacent hoops $25_i$ and $25_{i+1}$. These pins 28 and 29 are in addition to pins 23a, 23b, etc. used to form zig-zag members of the respective hoops of stent 30. Wire-segment bridging member 26 is extended between pins 28 and both ends are at least partially wrapped around the pins, preferably with enough tension to remove unwanted slack from the wire, although various amounts of slack may be maintained, depending on the desired rigidity, flexibility, and compressed diameter of stent 30.

To effect welds during manufacture of a stent of the present invention, and as shown in FIG. 5, ball weld cutting holes 29 may be formed in the mandrel providing access to the mandrel interior, the holes desirably positioned such that sections to be welded, such as aligned, adjacent struts 34 and 34A, lie approximately above the ball weld cutting holes. In this way, a laser may be focused into ball weld cutting holes 29 to: (i) remove excess wire extending past ball weld cutting holes 29 and around the pins, and (ii) weld the remaining wire segment between the aligned, adjacent struts of adjacent hoops as, for example, bridging member 26 between struts 34 and 34A. The connection between bridging member 26 and struts 34 and 34A may, instead of a weld, may be accomplished according to any other suitable attachment means, including without limitation, tying, suturing, gluing, and stapling, with the glue or sutures being absorbable or non-absorbable, and including the use of polymer-containing connections.

As further illustrated in FIG. 5, a stent 30 constructed in accordance with the present invention may further include the plurality of separate bridging members 26a–26N disposed in succession along the length of the stent. Each successive separate bridging member $26_i$ connects a successive pair of adjacent hoops along the axis of stent 30 to form a spine along the length of stent 30. The spine may be a continuous spine of helically-aligned bridging members, similar to the spine illustrated in FIG. 1, or may be constructed of a single bridging member connecting a plurality of hoops along the length of the stent. Alternatively, as shown in FIG. 5, each successive connecting member $26_i$ may be circumferentially offset from a preceding connecting member with respect to the axis of stent 30 to define a helical spine of disjointed connecting members, or a "floating" spine. Hoop members 33, 37 disposed at each end of stent 30 may have the apex sections that point outwardly from the stent disposed in common planes perpendicular to the axis of stent 30, such as apex sections 35' of hoop 34 along plane I, as shown in FIG. 5.

To make this transition from hoops other than perpendicular end hoops 33 and 37 to the end hoops, the successive lengths of struts in the end hoops may be reduced along the circumference of the hoops. Additionally, or in the alternative, the successive amount of interdigitation (overlap) between apex sections of adjacent hoops may increase along the circumference of end hoops 33 and 37 approaching the end of wire 24.

FIGS. 6A–6E illustrate stent 40, another exemplary embodiment of the present invention. In stent 40, adjacent hoops 42a . . . 42N are interdigitated with respect to one another. That is, oppositely directed apex sections 44A and 44B in respective adjacent hoops 42b and 42c, for example, overlap one another axially, or expressed another way, they intersect a common plane angularly disposed with respect to the axis of stent 40. Hoop members 42a . . . 42N also preferably have zigs substantially in phase circumferentially about stent 40. Stent 40 comprises a continuous series of similarly-oriented apex sections 44A arranged in a helix in which each hoop 42i comprises one 360-degree wrap of the helix. Each apex section in the helix comprises two struts attached thereto, in this embodiment with one strut being longer than the other to effect the helical progression. Such a hoop configuration is also seen in U.S. Pat. No. 5,575,816 to Rudnick et al., which is incorporated herein by reference and which illustrates a variety of other interdigitated stent configurations.

In a pair of adjacent hoops, such as hoops 42b and 42c, one strut 45 of hoop member 42b is aligned with and overlaps strut 45 of hoop member 42c, and is connected to form a connecting member 48a–N, preferably by spot welding, although other connection mechanisms are contemplated as will be understood by those skilled in the art. Interdigitated stent 40 in its normal tubular form is illustrated in FIG. 6E.

Figures 6A, 6B, 6C, 6D:
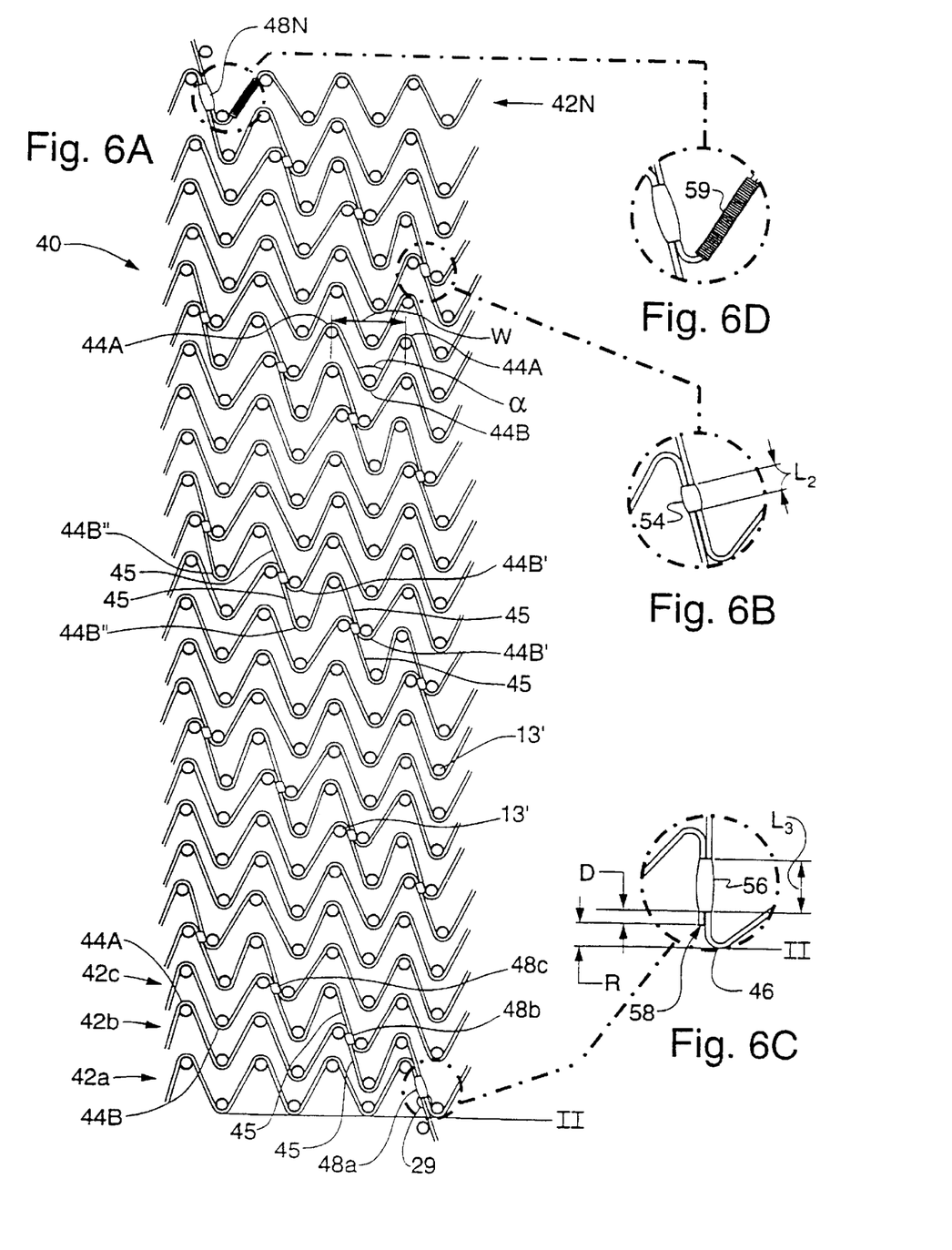
FIG. 6A is a diagrammatic view of an exemplary embodiment of a stent according to this invention having interdigitated zigs, where the tubular stent is shown opened along a line parallel to the stent axis, and flattened.
FIGS. 6B–6D are diagrammatic views of enlarged portions of the stent of FIG. 6A, showing an exemplary end weld, and exemplary middle weld, and an exemplary radiopaque marker, respectively.
Figure 6E:
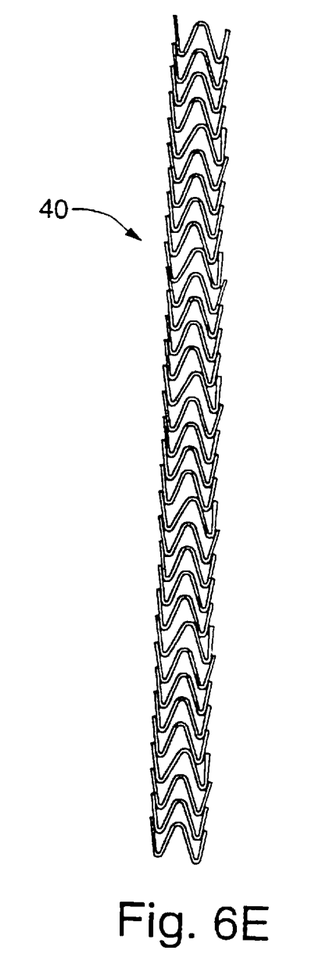
FIG. 6E is a diagrammatic view of an exemplary embodiment of stent 6A, where the stent is shown in its normal tubular configuration.
Figure 10:
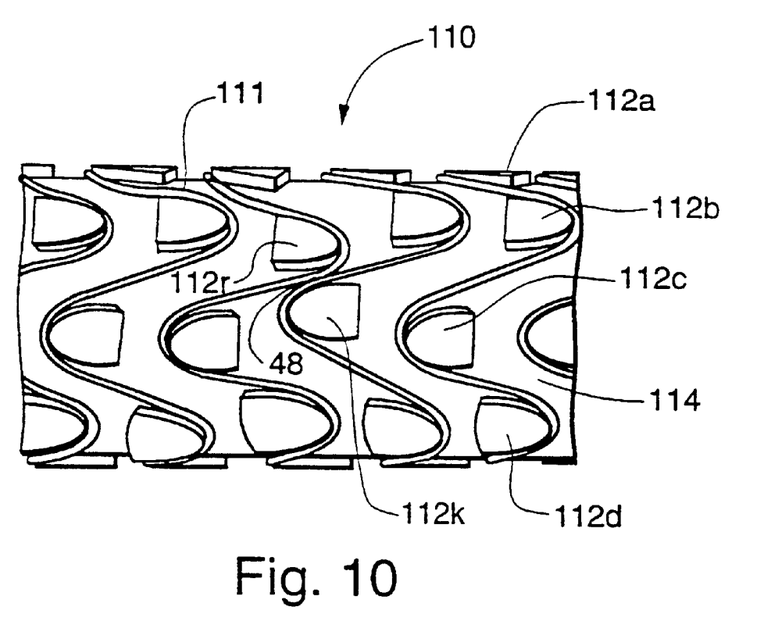
FIG. 10 is a partial diagrammatic view of the stent shown in FIG. 6A mounted on a mandrel during fabrication of the stent.

Referring now to FIG. 10, there is shown a helical stent 110, corresponding to the layout shown in FIG. 6A, on a tubular mandrel 114. Helical stent 110 or a helical segment thereof, as shown in FIG. 10, may be constructed by winding N filaments 111, where N is a whole number of at least 1, around N respective sets of pegs 112a–N on a tubular mandrel 114. As shown in FIG. 11, N=1. Each of the N sets includes at least three axially offset pegs, such as pegs 112a, 112b, and 112c, defining a zig-zag configuration at a preselected axial location on mandrel 114, with circumferentially successive pairs of pegs (pegs 112c and 112d, for example) being axially offset in a preselected direction from the pair which precedes it (pegs 112a and 112b) so as to form a helical zig-zag pattern repeatedly traversing the mandrel along the length of stent 110. Each traversal of a preselected angular portion of mandrel 114 by pegs 112a–N includes at least one common peg (112r, for example) approximately 360° helically offset from an adjacent peg (112k). The peg adjacent the common peg may be part of the same set of pegs (for instance, where N is equal to 1) or a part of a circumferentially adjoining set of pegs (where N is greater than 1). Common peg 112r provides at least one circumferential location in each traversal of a preselected angular portion, where a portion of the filament in each traversal of a preselected angular portion contacts a portion of a filament in an adjacent traversal. This contact may be with the same filament (for instance, where N is equal to 1 as shown in FIG. 11) or with an different filament (where N is greater than 1). A connection 48 is formed along the contacting adjacent filaments or portions thereof, forming a circumferential stent or segment thereof comprised of a helical succession of zig-zags. Thus, the wire configuration may form a helix as shown in FIGS. 6A, 6E, and 11, or a double- or other multiple-helix (not shown). As shown in FIG. 6A, a single filament (N=1) repeatedly traverses the mandrel (not shown) along a single set of pegs, wherein in each angular traversal of 450° there is a common peg 13' approximately (in this case slightly greater than) 360° offset from an adjacent peg 13' (the pegs immediately adjacent each connecting member 48a–N).

Stent 40 as shown in FIG. 6A comprises a plurality of connecting members 48a–N disposed in succession along the stent axis between pairs of adjacent hoops. Each set of connecting members 48a–N connects a successive pair of adjacent hoops along the axis of stent 40 to form a spine along the length of the stent. As with the successive connecting members 26 of FIG. 5, each pair of successive connecting members $48_i$ is circumferentially offset from a preceding connecting member $48_{i-1}$ with respect to the axis of stent 40.

As shown in FIG. 6A, each apex section 44B includes an apex angle α and a zig width W measured between adjacent, apex sections 44A opposite apex section 44B. As shown in FIG. 6A, the included angle (zig angle) and zig width of apex sections 44B are essentially uniform throughout stent 40, except for the apex sections 44B' and 44B" that include the struts 45 that form connecting members 48a–N. Apex sections 44B' and 44B" have a non-uniform zig angle and resulting zig width as compared to apex sections 44B. As shown in FIG. 6A, the zig including apex section 44B' has a greater included angle and has a greater zig width than the uniform angle and width included by apex sections 44B; apex section 44B" has a lesser included angle and smaller zig width than the uniform angle and width. As shown in FIG. 6A, stent 40 comprises a helical configuration having 4 zigs per 360-degree wrap, each such wrap comprising a hoop. Apex section 44B' is spaced 5 zigs from each preceding 44B'; apex section 44B" is similarly spaced 5 zigs from each preceding 44B". Thus, for a stent with N zigs, the non-uniform zigs are spaced every N+1 zigs to achieve the helical pattern of connections 48a–N as shown in FIG. 6A. In other words, for the 4-zig stent of 6A, connecting members 48a–N are uniformly distributed in a helical spacing approximately every 450° along the length of the stent to form a helical spine. Other helical or non-helical spine configurations may be achieved by spacing the non-uniform zigs differently.

FIGS. 6B and 6C illustrate exemplary spot weld configurations within stent 40. For adjacent, aligned struts 48b–$48_{N-1}$, the portion of each strut adjacent one another may be of a first length having a weld 54 of length $L_1$, as shown in FIG. 6B. For adjacent, aligned struts 48a and 48N on the end hoops, however, the portions of each strut adjacent one another may be longer, and thus may include a weld 56 of length $L_2$, as shown in FIG. 6B. To avoid sharp edges protruding from the stent, end strut 58 may be cut, as shown in FIG. 6C, so that it terminates a distance D from weld 56 in a position that lies short of plane II on which apex section 46 lies. For instance, the end of end strut 58 may be cut so that it terminates a distance above plane II equivalent to the radius R of apex section 46. As shown in FIG. 6A, end strut 58 has not yet been cut, but may be cut using ball weld cutting hole 29, similar to those described with reference to FIG. 5.

FIG. 6D illustrates an exemplary radiopaque marker 59 that may be used with the present invention. Marker 59 may comprise a radiopaque substance, such as a platinum wire, wrapped about a strut on an end hoops. This substance thus defines a surface having a different radiopacity than the area surrounding it. This same effect may be achieved by marking a particular location of the stent with an area of lower radiopacity. One or more markers 59 may be disposed on one or both of the end hoops. Marker 59 generally may be tightly wound with no underlying strut visible to the unaided eye, and may extend 1–2 wraps past the start of the radius where the strut bends to form the apex section. Marker 59 is typically configured without sharp edges at the ends.

Figure 6F:
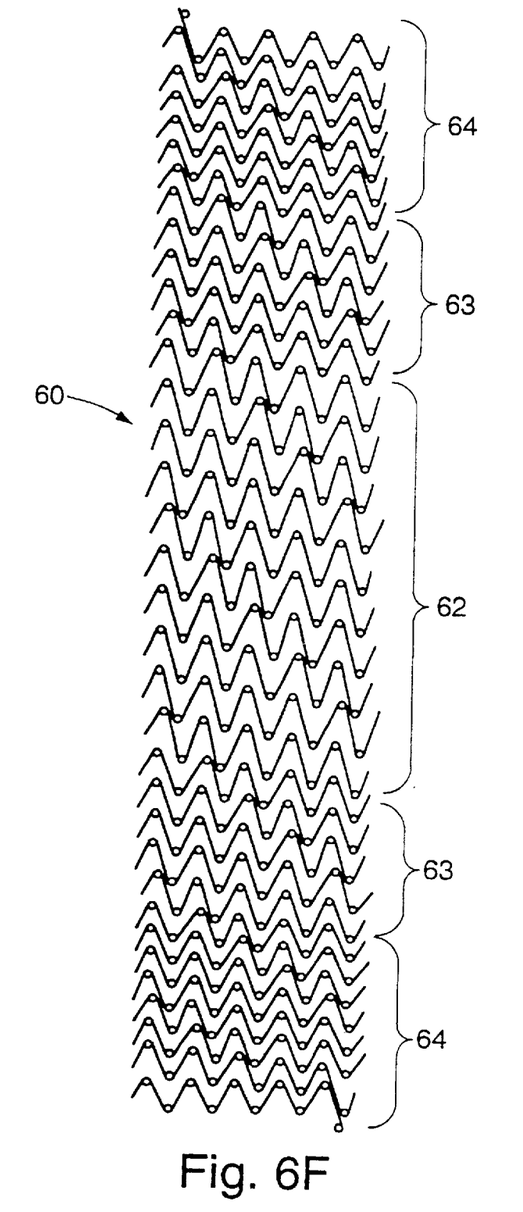
FIG. 6F is a diagrammatic view of an exemplary embodiment of a stent according to this invention having interdigitated zigs and a plurality of longitudinal sections of different zig configurations, where the tubular stent is shown opened along a line parallel to the stent axis, and flattened

FIG. 6F is a diagrammatic view of an exemplary embodiment of stent 60, opened along a line parallel to the stent axis and flattened, having interdigitated zigs, similar to stent 40 of FIGS. 6A–E, but additionally having a plurality of longitudinal sections, similar to stent 10C as shown in FIG. 4. Middle section 62 has a longer zig length than end sections 64, and transition sections 63 intermediate the middle section and each end section have a zig length that is between the length of the middle and the end section zigs.

Figure 7:
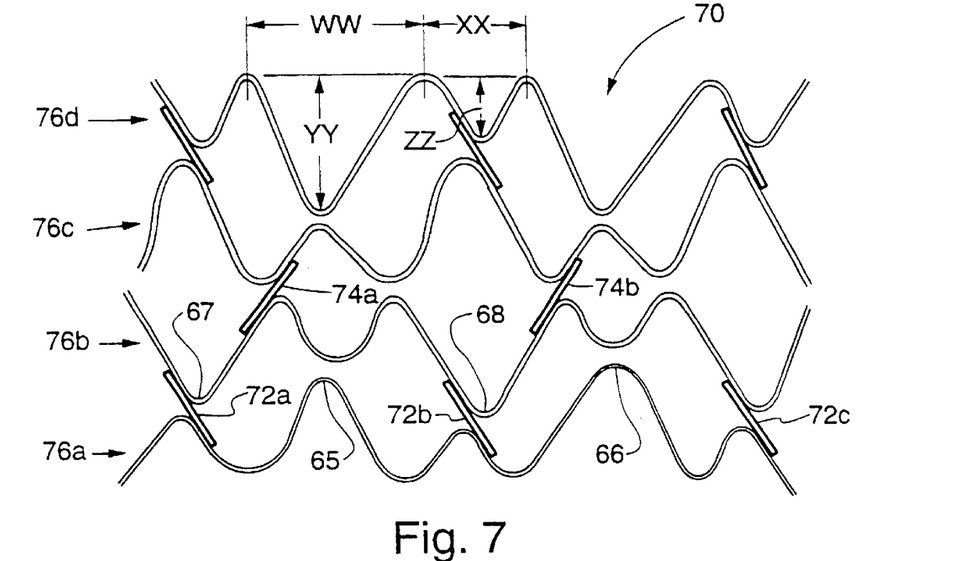
FIG. 7 is a partial side view of an exemplary embodiment of a stent according to this invention having alternating zig lengths, where the tubular stent is shown opened along a line parallel to the stent axis, and flattened.

FIG. 7 illustrates still another stent 70 constructed in accordance with the present invention. Stent 70 has been cut longitudinally and laid flat for purposes of illustration. Stent 70 is formed by winding a wire around pins extending from a mandrel somewhat similar to the manner described with reference to FIG. 1, although the pins are configured such that zig-zag sections of respective hoops 76a, 76b, 76c, 76d are of varying height and varying width. In the embodiment illustrated in FIG. 7, the width of the zig length alternates between distance XX and WW along each hoop circumferentially about stent 70. The zig length similarly alternates between length YY and ZZ moving along each hoop circumferentially about stent 70. Length ZZ is approximately half of length YY in FIG. 7, although other length variations are contemplated. Adjacent hoops, such as hoops 76a and 76b, are phase-shifted by approximately and 180 degrees and inverted with respect to one another. Accordingly, apex sections 65 and 66 of hoop member 76a pass through a plane perpendicular to the axis of stent 60 determined by the positions of oppositely directed alternate apex sections 67 and 68 in adjacent hoop 76b. The configuration of FIG. 7 may be incorporated into transition segments of other stents constructed according to the present invention.

A series of separate bridging members 72a, 72b, and 72c connects adjacent hoops 76a and 76b, as shown in FIG. 7. Another series of separate connecting members 74a and 74b connects adjacent hoops 62b and 62c. Bridging members 72a, 72b, and 72c are angled relative to the tubular axis of stent 70 in opposite orientations than bridging members 74a and 74b, to counter rotating effects in stents in which bridging members between successive pairs of adjacent hoops are oriented in the same direction. The number of bridging members may vary, depending on the desired implementation, as may the orientations of bridging members 72a, 72b, 72c, 74a and 74b.

Figure 8:
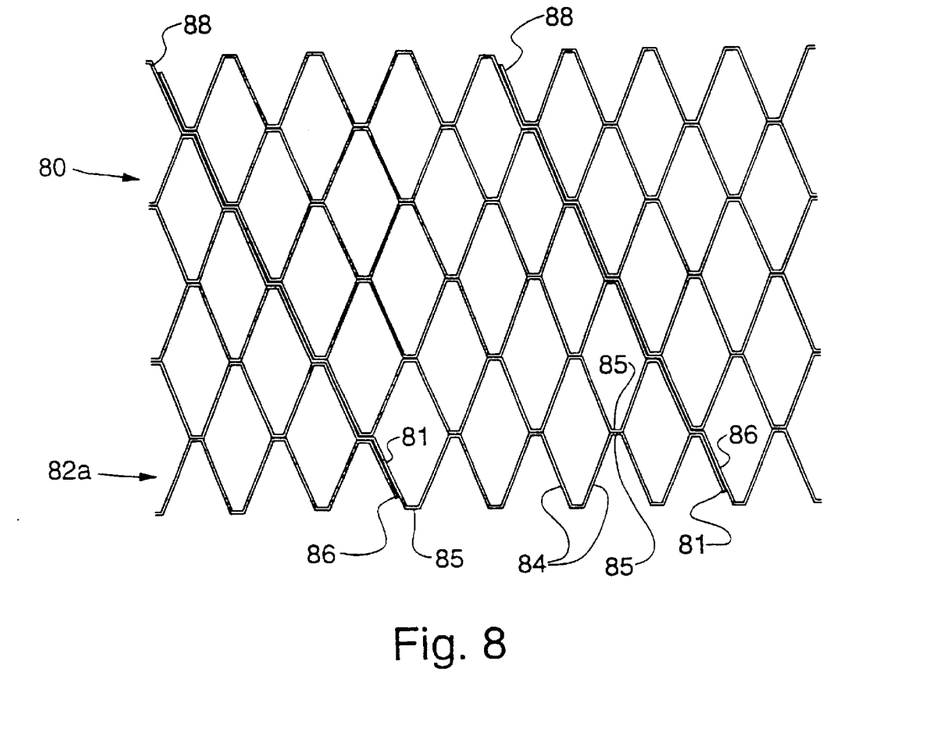
FIG. 8 is a partial diagrammatic view of another exemplary embodiment of a stent according to this invention having straight-edged apex sections, where the tubular stent is shown opened along a line parallel to the stent axis, and flattened.

Stent 80 of FIG. 8 is formed by winding a first wire 81 around pins (not shown) on a mandrel. The geometry of the pins may be substantially circular to produce rounded apex sections, as in FIG. 1, or have straight edges such as to produce apex sections having straight edges as in FIG. 8. In this manner, zig-zag members are formed and defined by a successive series of struts 84 connected by apex sections 85 alternately pointing in opposite axial directions. The winding continues in this manner around about half the circumference of stent 80. A second wire 86 is introduced and wound around the remaining circumference of stent 80 to complete a first hoop member 82a. Where wires 81 and 86 overlie one another, they may be spot or linearly welded, thus to produce a pair of helical spines lending integrity to stent 80.

Any of the variations described herein may be combined with any other variation described herein or known in the art, where practical, to develop a stent architecture according to the present invention. Such variations may be uniformly utilized throughout the length of the stent, or as shown in FIG. 6F, the stent may comprise a plurality of longitudinal sections, each of which may differ from another segment with respect to, for example without limitation: the size of one or more of the apex section angles, the apex section axial length, the number of apex sections per hoop, the number of connective spines, the spacing or offset between facing apex sections, the type of connecting member, and the uniformity of adjacent zigs. Moreover, the "struts" of each apex section and the connections therebetween may be straight, as in a jagged zig-zag configuration, or curved somewhat, such as when the overall stent section is more sinusoidal.

Although this invention has been described with reference to particular embodiments, it is not intended that this invention be limited thereto. Rather, the scope of the appended claims should be construed to cover all forms and variants of the invention as may be made by those skilled in the art without departing from the spirit and scope thereof.

What is claimed is:

1. A tubular stent having a tubular axis, said stent comprising a single continuous filament wound into a non-helical configuration to form a plurality of circumferential hoops linearly disposed in succession along said axis, each of said hoops comprising elements defined by a successive series of struts, each angled with respect to the stent tubular axis when the stent is in an expanded configuration, connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section, and said first and second struts are aligned with one another.

2. The stent according to claim 1 wherein each connecting member comprises a connector selected from the group consisting of: a spot weld, a continuous weld, an absorbable suture, a non-absorbable suture, a staple, absorbable glue, non-absorbable glue, and a polymer-containing connection.

3. The stent according to claim 1 wherein axially opposed apex sections of adjacent hoops are axially spaced from one another and said connecting member comprises a bridging member aligned with and connected to said first and second struts.

4. The stent according to claim 3 wherein each bridging member is connected to each of said first and second struts by a connector selected from the group consisting of: a spot weld, a continuous weld, an absorbable suture, a non-absorbable suture, a staple, absorbable glue, non-absorbable glue, and a polymer-containing connection.

5. The stent according to claim 3 wherein said bridging member and said struts connected thereto are comprised of the same material of construction and are of the same cross sectional dimensions.

6. The stent according to claim 3 wherein said bridging member comprises a portion of said single continuous filament.

7. The stent according to claim 1 wherein the single continuous filament comprises a material selected from the group consisting of: nitinol wire, stainless steel wire, and thermoplastic polymer.

8. The stent according to claim 1 comprising four to six similarly-oriented apex sections in each hoop.

9. The stent according to claim 1 in which all of said hoops have a similar number of similarly-oriented apex sections.

10. The stent of claim 1 wherein each apex section pointing in a first direction and two struts attached thereto comprise an element, the element length and element width of each adjacent element being uniform in each hoop.

11. The stent according to claim 1 having an diameter of 3–40 millimeters.

12. The stent according to claim 1 further comprising a graft layer enclosing at least a portion of the interior space defined by said stent.

13. The stent according to claim 1 wherein the apex sections have a geometry selected from the group consisting of: rounded or straight-edged.

14. The stent according to claim 1 further comprising at least one selected surface area, said selected surface area having a different radiopacity than the surface area surrounding said selected surface area.

15. The stent according to claim 1 wherein the elements have a zig-zag or sinusoidal configuration.

16. A tubular stent having a tubular axis, said stent comprising a single continuous filament wound into a non-helical configuration to form a plurality of circumferential hoops linearly disposed in succession along said axis and axially spaced from one another, each of said hoops comprising elements defined by a successive series of struts connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section, said first and second struts are aligned with one another, and one or both of said first and second struts are elongated, relative to remaining struts in said adjacent hoops, to lie adjacent one another for at least some axial distance to permit connection therebetween.

17. The stent according to claim 1 wherein the connecting members of adjacent pairs of hoops are arranged in a pattern to form a connective spine along the length of the stent.

18. The stent according to claim 17 wherein the connected struts forming said connective spine are aligned with one another helically along the length of said stent.

19. The stent according to claim 17 wherein the connected struts forming said connective spine are not aligned with one another along the length of said stent.

20. A tubular stent having a tubular axis, said stent comprising a single continuous filament wound into a non-helical configuration to form a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section, said first and second struts are aligned with one another, and each pair of adjacent hoops includes a plurality of paired struts in axially opposed apex sections, each of said strut pairs being connected to one another to form a plurality of connective spines along the length of said stent.

21. A tubular stent having a tubular axis, said stent comprising a single continuous filament wound into a non-helical configuration to form a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section, said first and second struts are aligned with one another, and the stent comprises at least two longitudinal segments, the hoops in at least one of said segments differing from those in another of said segments with respect one or more of: apex section included angles, element length, and number of apex sections per hoop.

22. A tubular stent having a tubular axis, said stent comprising a single continuous filament wound into a non-helical configuration to form a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section, said first and second struts are aligned with one another, and the stent comprises at least two longitudinal segments, each hoop in a first of said segments having a first element length and each hoop in a second of said segments having a second element length that is different from said first element length.

23. The stent according to claim 22 further comprising a transition segment between said first and second segments, each hoop in said transition segment having a third element length intermediate said first and second element lengths.

24. The stent according to claim 22 further comprising a transition segment between said first and said second segments, said transition segment having a plurality of element lengths that provide a gradual transition between said first and second element lengths.

25. A tubular stent having a tubular axis, said stent comprising a single continuous filament wound into a non-helical configuration to form a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section and said first and second struts are aligned with one another, each apex section pointing in a first direction and two struts attached thereto comprising an element, each element having a different element length, a different element width, or a combination thereof, with respect to each circumferentially adjacent element.

26. The stent of claim 25 wherein one or more selected elements of each hoop are connected to an element of an adjacent hoop with a bridging member.

27. The stent of claim 26 wherein the bridging members between selected elements of a first and second hoop are angled with respect to the stent tubular axis in a first direction and bridging members between selected elements of said second and a third hoop are angled with respect to the stent tubular axis in a second direction opposite said first direction.

28. A tubular stent having a tubular axis, said stent comprising a plurality of elements arranged in a helix, said elements defined by a successive series of struts connected by apex sections alternately pointing in first and second axial directions, the apex sections that point in the first direction axially overlapping the apex sections that point in the second direction on axially adjacent traversals of said helix, wherein at least a portion of a first of said struts of a first set of said apex sections that points in the first direction on a first traversal of said helix is aligned parallel to at least a portion of a second of said struts of a second set of said apex sections that points in the second direction on a second traversal, adjacent said first traversal, wherein said first strut and second strut portions are welded together to comprise a connecting member and less than all apex sections of said first set of apex sections are so aligned with apex sections of said second set of apex sections.

29. The stent of claim 28 further comprising a plurality of connecting members uniformly distributed along the stent according to a predetermined helical spacing.

30. The stent of claim 29 wherein the predetermined helical spacing is once approximately every 450 degrees.

31. The stent according to claim 28 wherein each apex section in said helix comprises two struts attached thereto, one strut being longer than the other.

32. The stent according to claim 28 wherein each apex section comprises an included angle, the apex sections being arranged in a pattern wherein the included angles are generally uniform except for selected apex sections in which the included angles are non-uniform to effect said alignment of said first and second struts.

33. The stent according to claim 28 wherein each apex section comprises an axial length, the axial lengths being generally uniform except for selected apex sections comprising one or both end hoops of said stent.

34. The stent according to claim 33 wherein said end apex sections define a plane perpendicular to said tubular axis at the end of said stent.

35. The stent according to claim 28 further comprising an end hoop disposed at each end of said stent in which apex sections that point outwardly from said stent lie in a common plane perpendicular to the axis of the stent.

36. The stent according to claim 35 wherein the elements of said end hoop have a progressively shorter axial length or amplitude leading to an end strut.

37. The stent according to claim 35 wherein the struts between apex sections of said end hoop progressively further overlap struts of an adjacent hoop leading to an end strut.

38. The stent according to claim 37 wherein the end hoops each comprise an end strut that is aligned adjacent to and connected to another strut of said end hoop.

39. The stent according to claim 38 wherein said end strut is connected to said another strut with a weld having a first weld length and said connecting members in said hoops that are not end hoops comprise a weld having a second weld length that is less than said first weld length.

40. The stent according to claim 39 wherein the end strut terminates short of said common plane perpendicular to the axis of the stent on which lie said end hoop apex sections that point outwardly from said stent.

41. A method of making a stent comprising,
 a) winding a first wire in a predetermined pattern about pins disposed on the surface of a mandrel conforming generally to the intended stent outer shape:
  i) transversely about the pins into a series of elements defined by a successive series of substantially straight sections connected by apex sections alternately pointing in opposite axial directions,
  ii) circumferentially about the mandrel to form at least two adjacent circumferential hoops of elements disposed axially in succession along the length of said stent,
 b) winding a second wire having end portions between a pair of weld segment pins disposed between proximate sections of said adjacent circumferential hoops, respectively,
 c) welding the end portions of the second wire to proximate sections of said adjacent circumferential hoops to define a weld segment connecting said adjacent circumferential hoops.

42. The method of claim 41 wherein step c) includes directing a laser through a hole formed in the mandrel to weld the end portions of the second wire to the first wire, to shorten the end portions of the second wire, or a combination thereof.

43. A method of making a stent comprising,
 first, winding a filament in a predetermined pattern around pins on a mandrel, said predetermined pattern including segments wherein a first portion of said filament lies adjacent a second portion of said filament at an area on said mandrel surface which includes an access hole to the interior of said mandrel, and,
 second, using said access hole to connect said first and second portions of said filament.

44. The method of claim 43 wherein said filamentary material is a wire and said access hole is used to connect said first and second filamentary portions by a weldment thereof.

45. A method of making a stent segment comprising (1) winding N filaments, where N is a whole number of at least 2, around N respective sets of pegs on a tubular mandrel, each of said N sets including at least three axially offset pegs at a preselected axial location on said mandrel, each of said sets including at least one common peg adjacent a circumferentially adjoining set, each of said filaments following a common path for a full distance between the common pegs of said circumferentially adjoining sets, and (2) forming a connection between said filaments along said common paths, and thus forming a circumferential stent segment comprising a succession of elements defined by a successive series of substantially straight sections connected by apex sections alternately pointing in opposite axial directions.

46. A method of making a stent comprising making an axial succession of circumferential stent segments, as recited in claim 45.

47. A method of making a stent segment comprising (1) winding N filaments, where N is a whole number of at least 1, around N respective sets of pegs on a tubular mandrel, each of said N sets including at least three axially offset pegs at a preselected axial location on said mandrel, circumferentially successive pairs of pegs being axially offset in a preselected direction from the pair which precedes it so as to form a helical pattern along the length of the stent segment, wherein in at least one circumferential location in each traversal of a preselected angular portion of the mandrel by said pegs there is a common peg approximately 360° offset from an adjacent peg of the same or a circumferentially adjoining set, adjacent which each filament contacts a portion of the same filament or an adjacent filament, and (2) forming a connection between said contacting adjacent filament portions, and thus forming a circumferential stent segment comprised of a helical succession of elements defined by a successive series of substantially straight sections connected by apex sections alternately pointing in opposite axial directions.

48. A tubular stent having a tubular axis, said stent comprising a plurality of circumferential hoops linearly disposed in succession along said axis, each of said hoops comprising elements defined by a successive series of struts connected by apex sections alternately pointing in opposite axial directions to form a continuous series of similarly-oriented apex sections that point in a first direction, said similarly-oriented apex sections arranged in a helix in which each hoop comprises one 360-degree wrap of said helix, at least one pair of adjacent hoops being connected to one another by a connecting member, said connecting member connecting a first strut, which is part of one of said connected adjacent hoops, to a second strut, which is part of the other of said adjacent hoops, wherein axially opposed apex sections of adjacent hoops are axially spaced from one another and said connecting member is a bridging member aligned with and connected to said first and second struts.

49. A tubular stent having a tubular axis, said stent comprising a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut, which is part of one of said connected adjacent hoops, to a second strut, which is part of the other of said adjacent hoops, said facing apex sections being circumferentially offset from one another such that said first and second struts are aligned, wherein axially opposed apex sections of adjacent hoops are axially spaced from one another and one or both of said first and second struts are elongated, relative to remaining struts in said adjacent hoops, such that said axially-opposed apex sections containing said first and second struts lie circumferentially adjacent one another for at least some axial distance to permit connection therebetween.

50. A tubular stent having a tubular axis, said stent comprising a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut, which is part of one of said connected adjacent hoops, to a second strut, which is part of the other of said adjacent hoops, said connected facing apex sections having a first circumferential offset from one another such that said first and second struts are aligned with one another, the stent having at least two longitudinal segments, the hoops in at least one of said segments differing from those in another of said segments with respect to one or more of: apex section included angle, element length, and number of apex sections per hoop.

51. A tubular stent having a tubular axis, said stent comprising a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut, which is part of one of said connected adjacent hoops, to a second strut, which is part of the other of said adjacent hoops, said stent comprising at least two longitudinal segments, at least one of said segments having a different number of continuous filaments and connective spines than a second of said segments.

52. A tubular stent having a tubular axis, said stent comprising a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut, which is part of one of said connected adjacent hoops, to a second strut, which is part of the other of said adjacent hoops, the stent comprising at least three longitudinal segments: a first segment in which each hoop has a first element length, a second segment in which each hoop has a second element length that is different from said first element length, and a transition segment between said first and second segments.

53. A tubular stent having a tubular axis, said stent comprising a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut, which is part of one of said connected adjacent hoops, to a second strut, which is part of the other of said adjacent hoops, each apex section pointing in a first direction and two struts attached thereto comprising an element, each element having a different element length, a different element width, or a combination thereof, with respect to each circumferentially adjacent element.

54. A tubular stent having a tubular axis, said stent comprising a plurality of circumferential hoops linearly disposed in succession along said axis, each of said hoops comprising elements defined by a successive series of struts connected by apex sections alternately pointing in opposite axial directions, at least one pair of adjacent hoops being connected to one another by a connecting member, said connecting member connecting a first strut connected to a first apex section, which is part of one of said connected adjacent hoops, to a second strut connected to a second apex section facing said first apex section, which is part of the other of said adjacent hoops, wherein said first apex section is circumferentially offset from said second apex section, said first and second struts are aligned with one another, said stent comprises a single continuous filament wound into a non-helical configuration to form said plurality of hoops, and said connecting member does not comprise a portion of said single continuous filament.

55. The stent of claim 54 wherein each strut is angled with respect to the stent tubular axis.

* * * * *